June 24, 1975 P. ECKE, JR. Plant Pat. 3,735
POINSETTIA PLANT
Filed April 22, 1974
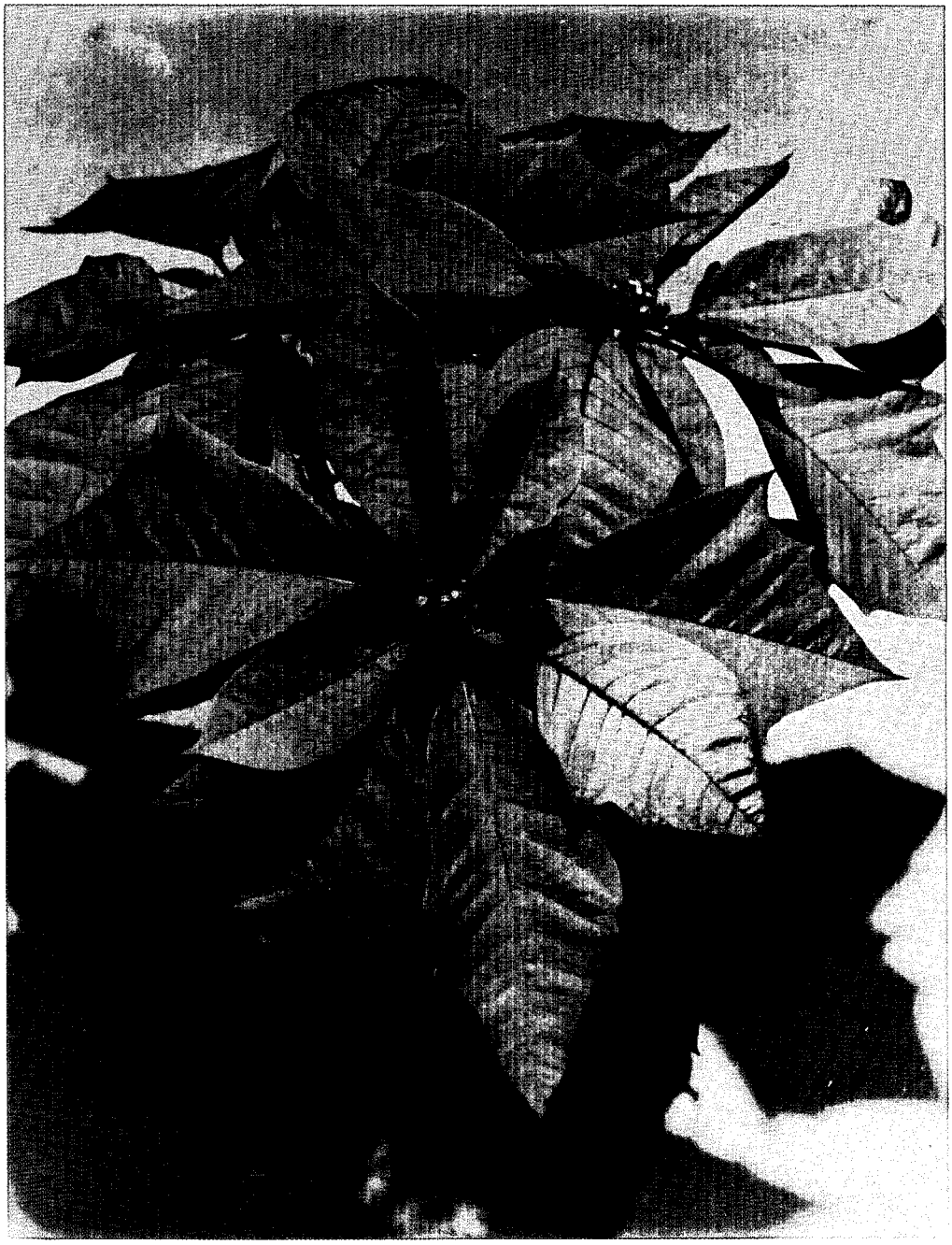

United States Patent

Plant Pat. 3,735

Patented June 24, 1975

3,735

POINSETTIA PLANT

Paul Ecke, Jr., Encinitas, Calif., assignor to Paul Ecke Ranch, Encinitas, Calif.

Filed Apr. 22, 1974, Ser. No. 462,995

Int. Cl. A01h 5/00

U.S. Cl. Plt.—86 1 Claim

ABSTRACT OF THE DISCLOSURE

The present invention relates to a new and distinct variety of poinsettia plant (botanically known as *Euphorbia pulcherrima*), which was originated by me by crossing two unnamed and unpatented red poinsettia seedlings.

The primary objectives of this breeding were to produce a new and improved poinsettia variety which has stiff stems that do not require staking, wider bracts than many other varieties heretofore known in commerce, a compact inflorescence form which creates an attractive effect in each bloom, and which retains its foliage and bracts for an unusually long period of time after reaching maturity. These objectives were fully achieved, along with other desirable improvements, as evidenced by the following unique combination of characteristics and which distinguish it from its parents, as well as from all other varieties of which I am aware:

(1) A very vigorous, tough, durable and tall plant habit, with the ability to grow well as a multiple stem and multiple bloom plant;
(2) A very vigorous and extensive root system;
(3) Stiff stems which do not require staking;
(4) Retention of the bracts, foliage and inflorescences for a long period of time after reaching maturity;
(5) A habit of not requiring light to delay bud set;
(6) A well-pinching habit which produces 3 or more breaks;
(7) A normal blooming habit at about 2° lower night temperatures than required for variety "C–1 Pink" (Plant Pat. No. 3,120) during the months of October, November and December, but having the ability to be satisfactorily brought into bloom and full maturity in every month of the year through the exercise of proper greenhouse cultural techniques;
(8) A distinctive and attractive appearance of the bracts and their absence of any tendency to droop with age;
(9) A distinctive and attractive Hot Pink general color tonality of the bracts;
(10) Absence of drooping and retention of the position of the inflorescences relative to the bracts without rising as occurs in other varieties as their inflorescences approach maturity; and
(11) Excellent keeping qualities and consequent suitability for home decoration.

Asexual reproduction of my new variety by vegetative cuttings propagated under mist at Encinitas, Calif., shows that the foregoing characteristics and distinctions come true to form and are established and transmitted through suceeding propagations.

The accompanying drawing shows a typical specimen plant of my new poinsettia variety as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious, as based on specimens grown at Encinitas, Calif.:

PARENTAGE: Seedling.

Seed parent—An unnamed red poinsettia seedling.

Pollen parent—An unnamed red poinsettia seedling.

PROPAGATION: Holds its distinguishing characteristics through succeeding propagations by vegetative cuttings.

FORM: Tall; upright; graceful contour.

HABIT OF GROWTH: Vigorous grower; tall.

ROOTING HABIT: Very fast (from 12 to 15 days under mist); vigorous; extensive; uniform.

BLOOMING HABIT: Approximately 10 weeks after start of short days.

BLOOMING SEASON: Naturally from October through December, but has excellent suitability for forcing in every month of the year by appropriate greenhouse culture practices; blooms well at about 2° lower night temperatures than required for the variety "C–1 Pink."

FOLIAGE: Alternate; borne horizontally on stems; persistent; normal abundance.

Size—Medium; borne on short petioles; from about 3 inches to 6 inches long; from about 2½ inches to 5 inches wide.

Shape—Little serration; wide at base and abruptly tapering to long point at tip.

Texture: Upper side—Medium glossy; medium smooth; with ordinary recessed veins. Under side—Dull; with ordinary protruding veins.

Margin—Well defined.

Color—Lighter green than either of the varieties "C–1 Pink" or "C–1 Red" (Plant Pat. No. 2,923).

DISEASE RESISTANCE: Resistant to rhizoctonia and pythium stem and root rot during propagation and growing period, and very resistant to botrytis during blooming period, as determined by comparison with other varieties grown under the same conditions at Encinitas, Calif., which are infected with these diseases.

BRACTS: Many (approximately 15 to 20 in number); very wide (up to 4 inches or more); excellent retention; new bracts form and develop as other bracts mature; very long lasting; retain relative position and do not droop when mature or as bracts continue to age; retain their color exceptionally well; have short petioles which give plant a full appearance; tight center giving inflorescence an attractive form and appearance.

Color—Hot Pink, corresponding from near Carmine, Plate 21/2 to Crimson, Plate 22/2 when viewed in natural light, but appearing darker when photographed as in accompanying drawing.

FLOWERS:

Borne—Continuously for several months; many flowers per stem in regular clusters in various stages of development; borne on strong, very short stems; slow development, giving a compact appearance for a greater period of time; position of the flowers remains relatively low without rising as they do in other commercial poinsettia varieties during early development, and flowers do not spread out during later stages of development, thereby presenting a more attractive appearance for a longer period of time.

Quantity of bloom—Relatively abundant; flowers gradually drop off after maturity; flower clusters remain tight but new ones do not continue to develop; centers do not spread.

Buds—From medium to large; borne on light green stems.

REPRODUCTIVE ORGANS:

Stamens—Few; from ⅛ inch to ¼ inch long. Color—Near Claret Rose, Plate 021.

Pollen: Color—Near Naples Yellow, Plate 403.

Styles: Color—Near Rose Opal, Plate 022.

Ovaries: Color—Near Lettuce Green, Plate 861.

Nectar cups: Color—Near Egyptian Buff, Plate 407.

GENERAL OBSERVATIONS: This new variety is generally similar to the variety "C–1 Pink" (Plant Pat.

No. 3,120) in respect to rooting time, branching ability, leaf retention and other features, but is particularly distinguished therefrom by its taller, more erect and less spreading habit of growth, with production of blooms in 10 weeks at night temperatures about 2° lower than required for "C–1 Pink," and particularly distinguished by its distinctive and attractive Hot Pink bract color.

I claim:

1. A new and distinct variety of poinsettia plant, substantially as herein shown and described, characterized particularly as to novelty by the unique combination of a very vigorous, tough, durable and tall plant habit, with the ability to grow well as a multiple stem and multiple bloom plant, a very vigorous and extensive root system, stiff stems which do not require staking, retention of the bracts, foliage and inflorescenses for a long period of time after reaching maturity, a habit of not requiring light to delay bud set, a well-pinching habit which produces 3 or more breaks, a normal blooming habit at about 2° lower night temperatures than required for variety "C–1 Pink" (Plant Pat. No. 3,120) during the months of October, November and December, but having the ability to be satisfactorily brought into bloom and full maturity in every month of the year through the exercise of proper greenhouse cultural techniques, a distinctive and attractive appearance of the bracts and their absence of any tendency to droop with age, a distinctive and attractive Hot Pink general color tonality of the bracts, absence of drooping and retention of the position of the inflorescences relative to the bracts without rising as occurs in other varieties as their inflorescenses approach maturity, and excellent keeping qualities and consequent suitability for home decoration.

No references cited.

ROBERT E. BAGWILL, Primary Examiner